United States Patent
Mizutani

[11] Patent Number: 5,613,960
[45] Date of Patent: Mar. 25, 1997

[54] DISPOSABLE BODY FLUIDS ABSORBENT PADDING

[75] Inventor: Satoshi Mizutani, Kawanoe, Japan

[73] Assignee: Uni-Charm Corporation, Ehime-ken, Japan

[21] Appl. No.: 459,998

[22] Filed: Jun. 2, 1995

[30] Foreign Application Priority Data

Jun. 3, 1994 [JP] Japan .................................. 6-122584

[51] Int. Cl.⁶ .................... A61F 13/15; A61F 13/20; A61F 13/48; A61F 13/50
[52] U.S. Cl. .................... 604/365; 604/358; 604/366; 604/378; 604/379; 604/380; 604/383; 604/385.1
[58] Field of Search .................... 604/358, 365, 604/366, 370, 372, 378, 379, 385.1, 380, 383

[56] References Cited

U.S. PATENT DOCUMENTS

| | | | |
|---|---|---|---|
| 2,788,003 | 4/1957 | Morin | 604/366 |
| 3,881,487 | 5/1975 | Schrading | 128/284 |
| 4,573,986 | 3/1986 | Minetola et al. | 604/366 |
| 4,798,603 | 1/1989 | Meyer et al. | 604/378 |

*Primary Examiner*—John G. Weiss
*Assistant Examiner*—Francis K. Cuddihy
*Attorney, Agent, or Firm*—Lowe, Price, LeBlanc & Becker

[57] ABSTRACT

A disposable body fluids absorbent padding is formed with a liquid-guiding fibrous sheet interposed between a liquid-permeable topsheet and a liquid-absorbent core. The fibrous sheet is intermittently fused to the topsheet in the direction of thickness as defined between the upper surface of the topsheet and the lower surface of the fibrous layer for improved fluid flow into the core.

6 Claims, 2 Drawing Sheets

DISPOSABLE BODY FLUIDS ABSORBENT PADDING

BACKGROUND OF THE INVENTION

The present invention relates to disposable body fluids absorbent padding and, more particularly, to a body fluids padding such as menstrual pads, diapers for infants, diapers for incontinence and the like.

It is well known in making such paddings that a topsheet is generally made from hydrophobic materials, wherein an inner surface thereof is covered with a liquid-guiding fibrous layer that is less hydrophobic than the topsheet or rather hydrophilic and in contact with a liquid-absorbent core in order to alleviate feelings of wetness by rapidly guiding discharged body fluids from the topsheet into the core. For example, Japanese Laid-Open Patent Application No. 1982-1340 discloses a technique wherein hydrophobic perforated plastic topsheet film is formed with adhesive on a lower surface thereof. Fibers which are less hydrophobic than the topsheet are flocked onto the adhesive to form a thin layer positioned against a liquid-absorbent core. In this manner, body fluids are more rapidly transferred to the core than in the case of the topsheet formed without the thin layer.

While the technique disclosed in the above-identified reference tends to bond the thin layer integrally to the topsheet with the adhesive applied to the lower surface, thereof depending on the thickness of the thin layer, the thin layer may have some portions which don't come into contact with adhesive consequently, such portions are not bonded to the topsheet or may even spaced from the topsheet. Should the body fluids absorbent padding be bent during actual use, component fibers of the thin layer will be loosened from one another or peeled off from the topsheet, causing flow disruption of the body fluids through capillary action at these seperations. Consequently, the body fluids will be prevented from being rapidly transferred to the core and will remain on the upper surface of the topsheet for a long duration, causing stuffiness or eruption. In addition, interruption of the passages will cause body fluids to leak sideways.

It is a principal object of the invention to solve such problems by integrally bonding the liquid-guiding fibrous layer to the topsheet by fusion of hot melt materials contained in both the topsheet and the liquid-guiding fibrous layer.

SUMMARY OF THE INVENTION

The object set forth above is achieved, according to the invention, by a disposable body fluids absorbent padding comprising a liquid-permeable topsheet, a liquid-impermeable backsheet, a liquid-absorbent core disposed therebetween and a liquid-guiding fibrous layer being more hydrophilic than the topsheet and interposed between the topsheet and the liquid-absorbent core to guide the body fluids from the topsheet into the core. Hot melt materials contained in both the topsheet and the liquid-guiding fibrous layer are fused at spots arranged intermittently in a plane of the topsheet thereby, the topsheet and liquid-guiding fibrous layer are integrally bonded together at these spots in the thickness direction as defined between the upper surface of the topsheet and the lower surface of the liquid-guiding fibrous layer.

The disposable body fluids absorbent padding constructed as described above is advantageous in that, during actual use, the component fibers of the liquid-guiding fibrous layer are neither loosened from one another nor peeled off from the lower surface of the topsheet, since the topsheet and the liquid-guiding fibrous layer are integrally bonded to each other in the direction of thickness by fusion of the hot melt material contained in both.

PREFERRED EMBODIMENTS OF THE INVENTION

Figure 1:
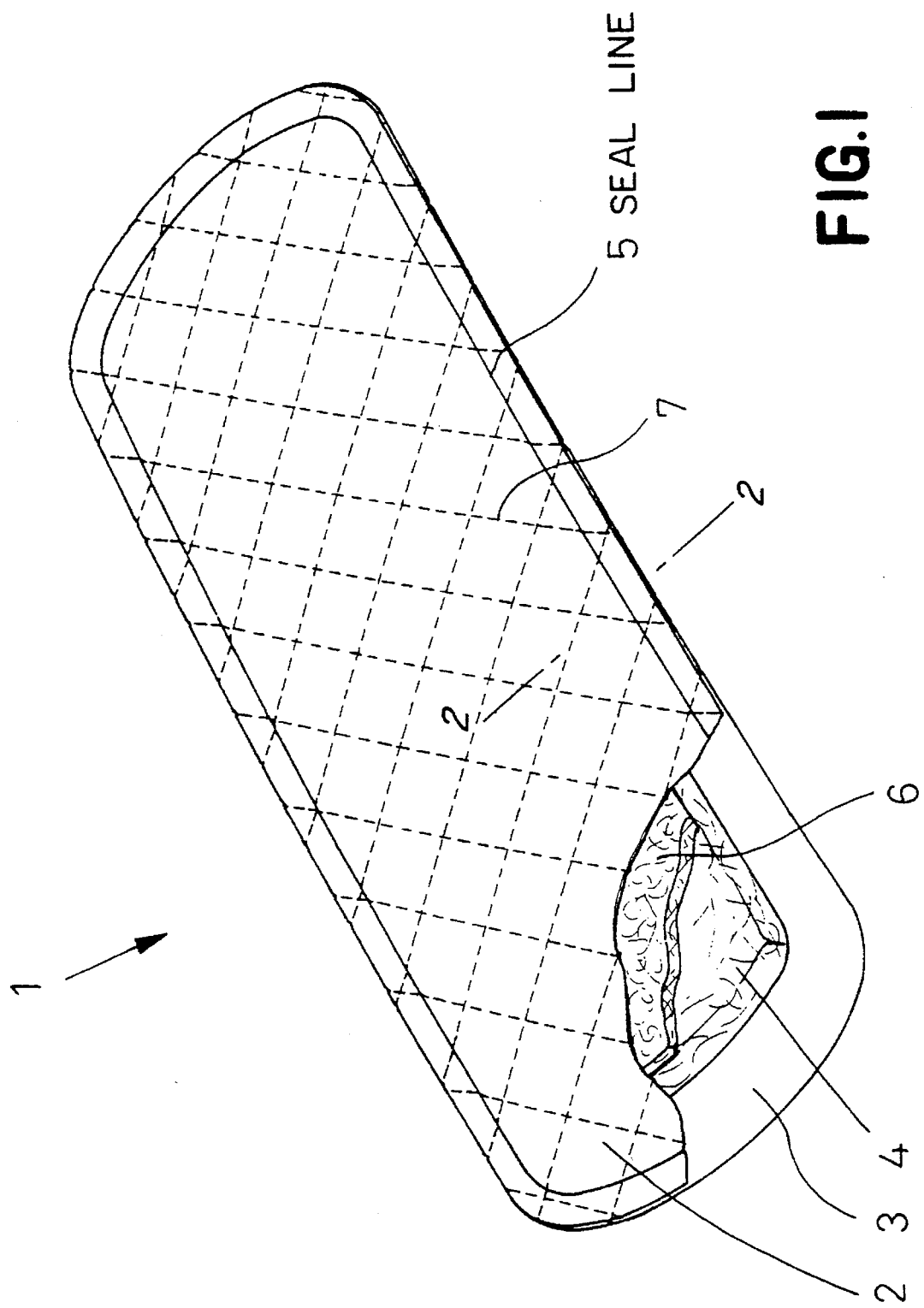
FIG. 1 is a perspective view of an embodiment of the invention in the form of a menstruation pad, partially broken away to reveal the interior construction thereof.

Referring to FIG. 1, a menstruation pad 1 comprises a liquid-permeable topsheet 2, a liquid-impermeable backsheet 3 and a liquid-absorbent core 4 disposed therebetween top and backsheets 2, 3 are water-tightly bonded together along a seal line 5 so that portions thereof extend outward beyond a peripheral edge of the core 4. As described below, a liquid-guiding fibrous layer 6 is bonded to the lower (i.e., not skin-contacting) surface of the topsheet 2 and disposed against the core 4. A plurality of fused spots 7 are formed in the upper surface of topsheet 2 in a lattice pattern. The topsheet 2 is preferably made of a hydrophobic sheet containing therein hot melt materials, specifically a nonwoven fabric containing 5% by weight or higher of thermoplastic synthetic fibers, split yarns fibrillated from a thermoplastic synthetic resin film or a mixture thereof, or a liquid-permeable perforated thermoplastic synthetic resin film. The fibrous layer 6 comprises suitable fibrous materials such as a nonwoven fabric containing 5% by weight or higher of hot melt fibrous materials, inclusive of split yarns, and is less hydrophobic than the topsheet 2. The fibrous layer 6 is also lower than the topsheet 2 in fibrous density and higher in cushioning effect. While fibrous materials similar to those of the topsheet 2 may be used to form the fibrous layer 6, such fibrous materials are preferably subjected to an appropriate treatment so as to be less hydrophobic than the topsheet, i.e., so as to become rather hydrophilic.

Figure 2:
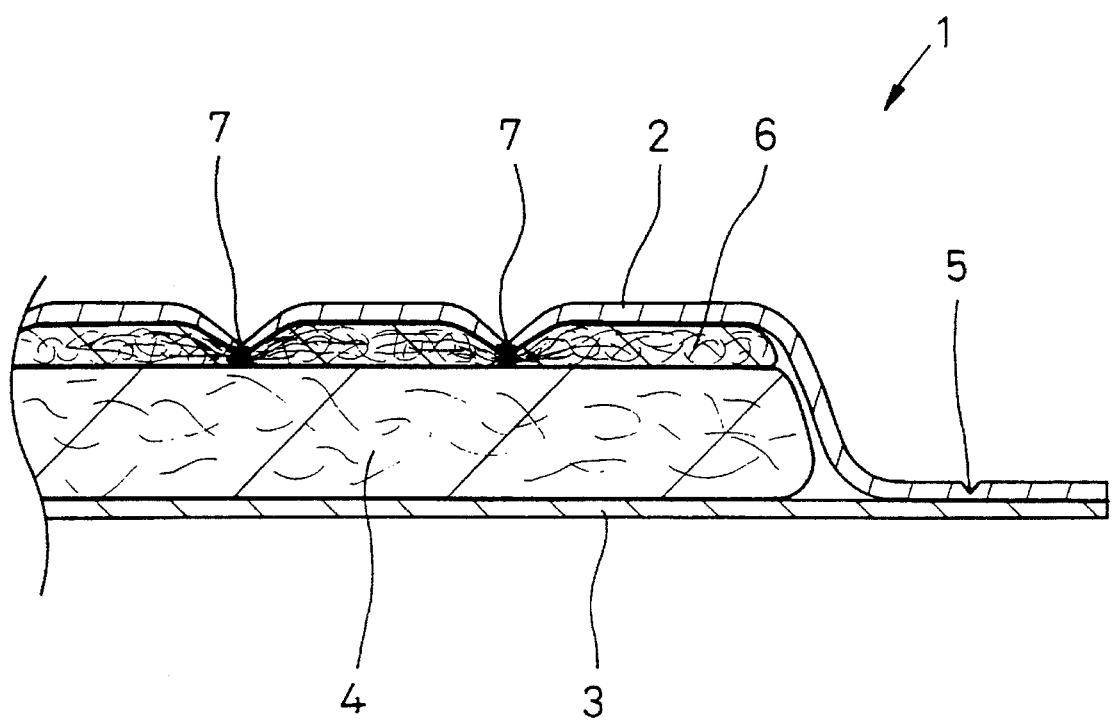
FIG. 2 is a sectional view taken along a line 2—2 in FIG. 1.

Referring to FIG. 2, the topsheet 2 and the fibrous layer 6 are integrally bonded together in the direction of thickness through the fused spots 7 extending between the upper surface of the topsheet and the lower surface of the fibrous sheet by fusion of hot materials contained in both the, topsheet and fibrous layer. Consequently, the component fibers of these topsheet 2 and fibrous layer 6 are neither loosened nor peeled off from one another at and adjacent the fused spots 7, independently of their thicknesses. A distance between each pair of adjacent fused spots 7 may be appropriately selected not only to maintain the topsheet 2 and the fibrous layer 6 in close contact with each other but also to maintain their component fibers reliably intertwined, respectively. Each of the fused spots 7 is compressed to have a high density and to form a groove along which the body fluids may diffusively flow and be rapidly guided into the core 4. In this manner, the core 4 is optimally utilized.

With pad 1, menstrual blood discharged onto the upper surface of the topsheet 2 is guided into the relatively hydrophilic fibrous layer 6 immediately underlying the topsheet 2 and then transferred into the core 4. The fibrous layer 6 functions to transfer the menstrual blood into the core 4 under the capillary action provided by its component fibers. The fused spots 7 assure that this capillary flow action is not interrupted in the direction of thickness by maintaining the upper surface of the fibrous layer 6 in close contact with the lower surface of the topsheet 2 and at the same time by maintaining the component fibers of the fibrous layer 6 reliably intertwined between the upper and lower surfaces of the fibrous layer 6.

The hot melt materials as the components of the topsheet 2 and the fibrous layer 6 may be a film or fibers, for example, of polyethylene, polypropylene, nylon, polyester resin or composite fibers thereof. Alternatively, hydrophilic materials such as rayon fibers or pulp fibers up to 20% by weight may be mixed into the above-mentioned materials. The backsheet 3 and the liquid-absorbent core 4 are made of customary materials. To fuse topsheet 2 and fibrous layer 6 together, a conventional technique such as heat embossing may be used in a pattern of spots as presented by the fused spots 7 in FIGS. 1 and 2, or straight lines, curved lines or combination of these lines and spots.

The disposable body fluids absorbent padding 1 according to the invention is advantageous in that the topsheet and the liquid-guiding fibrous layer are never peeled off from each other and the component fibers contained in the sheet and layer are never loosened from one another independently of their thicknesses, since the fibrous layer interposed between the topsheet and the liquid-absorbent core is integrally bonded to the topsheet in the direction of their thicknesses. Accordingly, even if the padding is bent or wrinkled during use, the body fluids can be rapidly transferred from the upper surface of the topsheet into the liquid-absorbent core without occurrence of sideway leakage.

What is claimed is:

1. A disposable body fluids absorbent padding comprising a liquid-permeable topsheet, a liquid-impermeable backsheet, a liquid-absorbent core disposed between said topsheet and backsheet and a liquid-guiding fibrous layer being more hydrophilic than said topsheet and interposed between said topsheet and said liquid-absorbent core to guide the body fluids from said topsheet into said core, wherein:

hot melt materials contained in both said topsheet and said liquid-guiding fibrous layer, respectively, are fused at a plurality of spots arranged intermittently in a plane of said topsheet whereby said topsheet and said liquid-guiding fibrous layer are integrally bonded together at said spots in a direction of thickness of said padding, said fused spots extending between an upper surface of said topsheet and a lower surface of said liquid-guiding fibrous layer.

2. A disposable body fluids absorbent padding according to claim 1, wherein said fused spots are arranged in a lattice pattern.

3. A disposable body fluids absorbent padding according to claim 1, wherein said plurality of intermittent fused spots form fused lines.

4. A disposable body fluids absorbent padding according to claim 1, wherein each of said fused spots is compressed to have a high density and to form a groove.

5. A disposable body fluids absorbent padding according to claim 1, wherein said topsheet and backsheet are bonded together along a seal line so that peripheral portions thereof extend outward beyond a peripheral edge of both the core and said seal line, and wherein said fused spots are also formed outwardly of the peripheral edge of the core to at least said seal line.

6. A disposable body fluids absorbent padding comprising a liquid-permeable topsheet, a liquid-impermeable backsheet, a liquid-absorbent core disposed between said topsheet and backsheet and a liquid-guiding fibrous layer being more hydrophilic than said topsheet and interposed between said topsheet and said liquid-absorbent core to guide the body fluids from said topsheet into said core, wherein:

hot melt materials contained in both said topsheet and said liquid guiding fibrous layer, respectively, are fused along fusing lines which in plan view form a lattice pattern, whereby said topsheet and said liquid guiding fibrous layer are integrally bonded together along said fusing lines in a direction of thickness of said padding, said fusing lines extending between an upper surface of said topsheet and a lower surface of said liquid guiding fibrous layer.

\* \* \* \* \*